United States Patent
Thiele

(10) Patent No.: US 9,880,271 B2
(45) Date of Patent: Jan. 30, 2018

(54) ULTRASONIC THICK SLICE IMAGE FORMING VIA PARALLEL MULTIPLE SCANLINE ACQUISITION

(75) Inventor: Karl Thiele, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2161 days.

(21) Appl. No.: 12/594,885

(22) PCT Filed: Apr. 9, 2008

(86) PCT No.: PCT/IB2008/051346
§ 371 (c)(1),
(2), (4) Date: Oct. 6, 2009

(87) PCT Pub. No.: WO2008/126015
PCT Pub. Date: Oct. 23, 2008

(65) Prior Publication Data
US 2010/0168580 A1    Jul. 1, 2010

Related U.S. Application Data

(60) Provisional application No. 60/911,580, filed on Apr. 13, 2007.

(51) Int. Cl.
*A61B 8/00* (2006.01)
*G01S 7/52* (2006.01)
(Continued)

(52) U.S. Cl.
CPC ...... *G01S 7/52085* (2013.01); *G01S 7/52095* (2013.01); *G01S 15/8925* (2013.01);
(Continued)

(58) Field of Classification Search
CPC ...................................... A61B 8/483
(Continued)

(56) References Cited

U.S. PATENT DOCUMENTS

| 4,350,917 A | 9/1982 | Lizzi et al. |
| 4,649,927 A | 3/1987 | Fehr et al. |

(Continued)

FOREIGN PATENT DOCUMENTS

| JP | 5344975 | 12/1993 |
| JP | 7178085 A | 7/1995 |

(Continued)

OTHER PUBLICATIONS

Gobbi, D.G., et al., "Interactive Intra-Operative 3D Ultrasound Reconstruction and Visualisation," Lecture Notes in Computer Science, Springer Verlag, Berlin, DE, vol. 2489, Jan. 1, 2002, pp. 156-163, XP002268190.

(Continued)

*Primary Examiner* — Serkan Akar

(57) ABSTRACT

An ultrasonic diagnostic imaging system scans a plurality of planar slices in a volumetric region which are parallel to each other. Following detection of the image data of the slices the slice data is combined by projecting the data in the elevation dimension to produce a "thick slice" image. Combining may be by means of an averaging or maximum intensity detection or weighting process or by raycasting in the elevation dimension in a volumetric rendering process. Thick slice images are displayed at a high frame rate of display by combining a newly acquired slice with slices previously acquired from different elevational planes which were used in a previous combination. A new thick slice image may be produced each time at least one of the slice images is updated by a newly acquired slice. Frame rate is further improved by multiline acquisition of the slices.

18 Claims, 5 Drawing Sheets

(51) Int. Cl.
*G01S 15/89* (2006.01)
*A61B 8/08* (2006.01)

(52) U.S. Cl.
CPC .......... *G01S 15/8993* (2013.01); *A61B 8/483* (2013.01); *G01S 7/52065* (2013.01); *G01S 15/8918* (2013.01); *G01S 15/8934* (2013.01)

(58) Field of Classification Search
USPC ........ 382/128; 600/437, 439, 440, 441, 443, 600/445, 447, 455, 458
See application file for complete search history.

(56) References Cited

U.S. PATENT DOCUMENTS

| | | | |
|---|---|---|---|
| 5,318,033 A | 6/1994 | Savord | |
| 5,438,994 A | 8/1995 | Starosta et al. | |
| 5,501,219 A * | 3/1996 | Phelps et al. | 600/442 |
| 5,617,863 A | 4/1997 | Roundhill et al. | |
| 6,015,384 A * | 1/2000 | Ramamurthy et al. | 600/440 |
| 6,059,727 A * | 5/2000 | Fowlkes et al. | 600/443 |
| 6,135,956 A | 10/2000 | Schmiesing et al. | |
| 6,436,048 B1 * | 8/2002 | Pesque | 600/447 |
| 6,447,453 B1 | 9/2002 | Roundhill et al. | |
| 6,464,638 B1 | 10/2002 | Adams et al. | |
| 6,471,650 B2 * | 10/2002 | Powers et al. | 600/447 |
| 6,491,636 B2 | 12/2002 | Chenal et al. | |
| 6,530,885 B1 * | 3/2003 | Entrekin et al. | 600/437 |
| 6,623,432 B2 * | 9/2003 | Powers et al. | 600/447 |
| 6,645,147 B1 * | 11/2003 | Jackson et al. | 600/458 |
| 6,669,641 B2 * | 12/2003 | Poland et al. | 600/447 |
| 6,692,438 B2 * | 2/2004 | Skyba et al. | 600/440 |
| 6,709,394 B2 * | 3/2004 | Frisa et al. | 600/445 |
| 6,716,174 B1 * | 4/2004 | Li | 600/447 |
| 6,749,569 B1 * | 6/2004 | Pellegretti | 600/441 |
| 6,755,788 B2 * | 6/2004 | Demers et al. | 600/447 |
| 6,761,689 B2 * | 7/2004 | Salgo et al. | 600/447 |
| 7,037,264 B2 * | 5/2006 | Poland | 600/447 |
| 7,097,619 B2 * | 8/2006 | Von Behren et al. | 600/447 |
| 7,131,947 B2 * | 11/2006 | Demers | 600/447 |
| 7,270,634 B2 * | 9/2007 | Scampini et al. | 600/447 |
| 7,578,791 B2 * | 8/2009 | Rafter | 600/447 |
| 7,645,237 B2 * | 1/2010 | Frisa et al. | 600/447 |
| 7,753,850 B2 | 7/2010 | Averkiou et al. | |
| 7,912,259 B2 * | 3/2011 | Arditi et al. | 382/128 |
| 8,177,718 B2 | 5/2012 | Savord | |
| 2002/0045826 A1 * | 4/2002 | Powers et al. | 600/447 |
| 2002/0045827 A1 * | 4/2002 | Powers et al. | 600/447 |
| 2003/0097068 A1 | 5/2003 | Hossack et al. | |
| 2004/0064044 A1 * | 4/2004 | Brock-Fisher | 600/437 |
| 2004/0064048 A1 * | 4/2004 | Li | 600/447 |
| 2005/0049479 A1 | 3/2005 | Brandl et al. | |
| 2005/0075567 A1 | 4/2005 | Skyba et al. | |
| 2005/0090745 A1 | 4/2005 | Steen | |
| 2005/0148874 A1 * | 7/2005 | Brock-Fisher et al. | 600/447 |
| 2005/0171430 A1 | 8/2005 | Zhang et al. | |
| 2006/0264754 A1 * | 11/2006 | Frisa et al. | 600/447 |
| 2007/0276239 A1 * | 11/2007 | Rafter | 600/437 |
| 2008/0015439 A1 * | 1/2008 | Raju et al. | 600/455 |
| 2010/0056921 A1 * | 3/2010 | Rafter et al. | 600/447 |
| 2010/0160780 A1 * | 6/2010 | Swan et al. | 600/439 |
| 2010/0168580 A1 * | 7/2010 | Thiele | 600/447 |
| 2011/0208061 A1 * | 8/2011 | Chang | 600/458 |

FOREIGN PATENT DOCUMENTS

WO 0169282 A 9/2001
WO 2005099579 A 10/2005

OTHER PUBLICATIONS

Welch, J.N., et al., "A Real-Time Freehand 3D Ultrasound System for Image-Guided Surgery," Ultrasonics Symposium, 2000 IEEE Oct 22-25, 2000, Piscataway, NJ, USA, IEEE, vol. 2, Oct. 22, 2000, pp. 1601-1604, XP010540921.

Li, P-C, et al., "Elevational Spatial Compounding," Ultrasonic Imaging, Dynamedia Inc., Silver Spring, MD, US, vol. 16, No. 3, Jul. 1, 1994, pp. 176-189, XP002261761.

* cited by examiner

ULTRASONIC THICK SLICE IMAGE FORMING VIA PARALLEL MULTIPLE SCANLINE ACQUISITION

This invention relates to medical diagnostic ultrasound systems and, in particular, to ultrasound systems which acquire and display an image from image data in the elevational dimension at high frame rates of display.

Ultrasonic diagnostic imaging is an imaging modality which forms images of coherent signal information. The nature of the coherent ultrasonic signals used, like the monochromatic lightwaves used for holographic imaging, results in constructive and destructive interference of the waves in the medium being imaged. As a result, the image contains noise in the form of a random mottling of the image known as "speckle." Since the speckle pattern of an image is constant and does not vary with time, the common approach to reducing the effect is to combine uncorrelated image data and reduce the speckle by an averaging effect proportional to the square root of two. The types of uncorrelated data used are typically data that are of different frequencies or acquired from different look directions, commonly known as frequency compounding (see, e.g., U.S. Pat. No. 4,350,917 to Lizzi et al.) and spatial compounding (see, e.g., U.S. Pat. No. 4,649,927 to Fehr et al.)

U.S. Pat. No. 6,464,638 to Adams et al. describes a new approach to spatial compounding which makes good utilization of probes designed for three dimensional imaging. In the Adams et al. technique a 3D imaging probe acquires images of planes which are substantially parallel to each other in the elevational dimension, the dimension normal to the image plane. In a typical implementation, Adams et al. use a probe with electronic beam steering and focusing in both azimuth and elevation to acquire not only an image of the slice plane of interest but also image planes parallel to that slice plane. The slices are then combined elevationally and the at least minimally uncorrelated data in the elevational dimension effects speckle reduction by spatial compounding in the elevational dimension.

While the implementation described in Adams et al. utilizes parallel processing to acquire multiple scanlines from a single transmit interval, it is nonetheless necessary to acquire a full data set of the elevational slices before a spatially compounded image can be formed. This is longer than the time required to acquire a single uncompounded slice image and hence the frame rate of display of the real time sequence will be slower than the frame rate of uncompounded real time imaging. Accordingly it is desirable to be able to produce spatially compounded images at higher real time frame rates of display.

In accordance with the principles of the present invention, a diagnostic ultrasound system and method are described which produces spatially compounded images from data in the elevational dimension at high frame rates of display. A plurality of slices are scanned with a 3D imaging probe which are substantially parallel in the elevational dimension. Following the acquisition of a new slice, the image data of the new slice is combined in the elevation dimension with the image data of previously acquired slices, then displayed. Various techniques can be used to combine the elevation data such as averaging, weighting or maximum intensity projection. A new spatially compounded image frame is produced for display in less time than is required to acquire the total number of slices being combined. In an illustrated implementation the frame rate of display is further increased by multiline acquisition of scanlines from several elevational slices at the same time.

Figure 1:
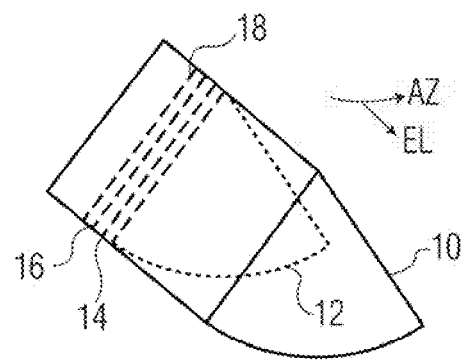
FIG. 1 illustrates a plurality of sector slices acquired in the elevational direction.

Referring first to FIG. 1, a volumetric region 10 is shown in perspective. In this example the volumetric region 10 is sector-shaped and contains a plurality of planar sector-shaped areas which are referred to herein as "slices." Four slices 12-16 are illustrated in this example. The slices are oriented parallel to each other in the elevation direction with their azimuth and elevation dimensions indicated to the right of the drawing. Each slice may be scanned by an array transducer located above the volumetric region by transmitting successive scanlines across a slice 12-16 in the azimuth direction and progressing from slice to slice in the elevation direction.

Figure 2:
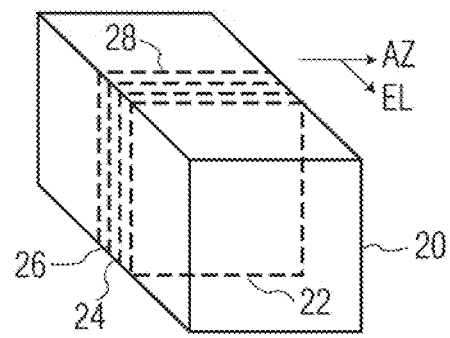
FIG. 2 illustrates a plurality of rectilinear slices acquired in the elevational direction.

FIG. 2 illustrates a rectilinear volumetric region 20 which also includes a plurality of slices oriented in parallel in the elevation direction. Four such slices 22-28 are shown in the drawing. These slices may be scanned in the same manner as the slices of FIG. 1 by a transducer array located above the volumetric region 20. In this example the slices are scanned by parallel scanlines in the azimuth direction rather than by angularly incremented scanlines from a common origin as is the case in the example of FIG. 1.

Figure 3:
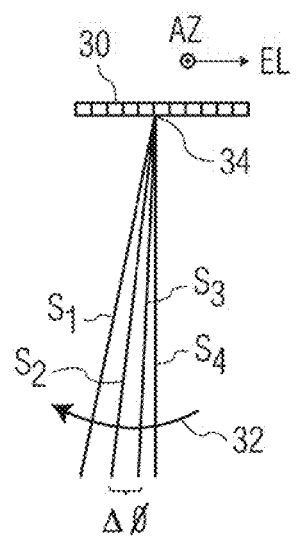
FIG. 3 illustrates a plurality of slices which are at different angular increments in the elevational direction.

FIG. 3 provides another example of slices of a volumetric region. These slices are of a pyramidal volumetric region with an apex 34 at the top of the volume. In this example four sector-shaped slices $S_1$-$S_4$ are shown in an "edge-on" view. That is, the elevation direction of the slices is indicated by the arrow 32, and the azimuth direction is into the plane of the drawing. The azimuth and elevation directions with respect to the array transducer 30 are shown above the transducer array. In this example neighboring elevation slices are separated by an angular increment $\Delta\varphi$.

In each of these examples a single slice of a volume may be scanned and displayed. But in accordance with the principles of the present invention, a plurality of slices which are elevationally aligned are scanned and their data combined to form an image for display. Since each of the elevationally distinct slices is scanned by scanlines having different transmit-receive signal paths, each of the slices will exhibit its own unique speckle pattern. By combining the image data of a plurality of slices which define a thickness in the elevation dimension, the speckle artifact of the combined image will be reduced.

Figure 4A:
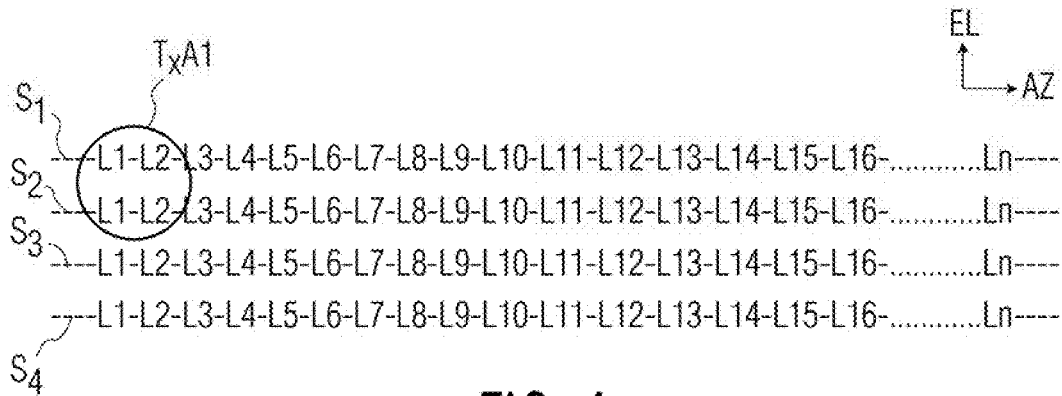
FIGS. 4a-4c illustrate the acquisition of multiple slices simultaneously by multiline acquisition in accordance with the principles of the present invention.
Figure 4B:
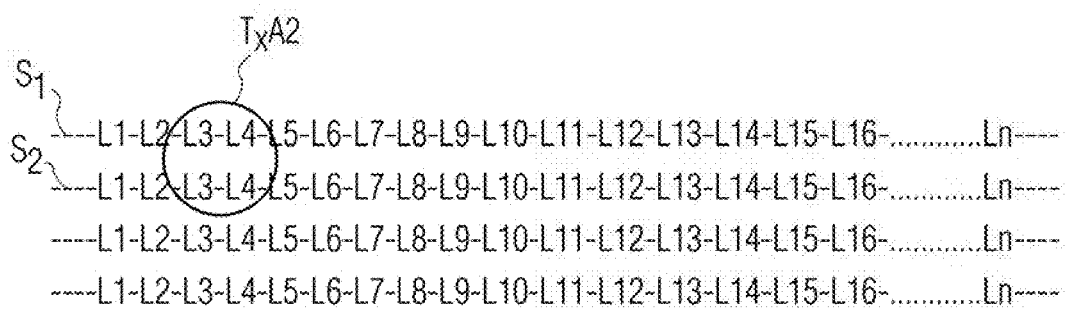
Figure 4C:
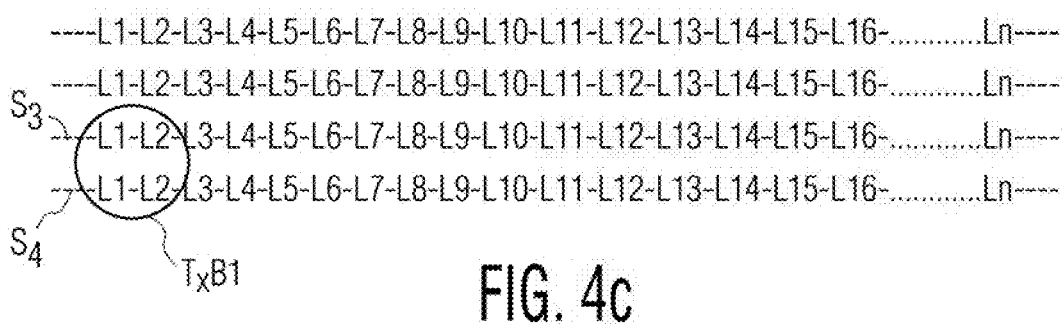

In accordance with a further aspect of the present invention, the slices may be scanned at a high speed by multiline acquisition. In multiline acquisition, one transmit beam insonifies multiple receive line locations and multiple receive lines are acquired in response to the single transmit event. FIGS. 4a-4c provide an example of multiline acquisition of four slices $S_1$-$S_4$ which are arranged in parallel in the elevational dimension. Each slice is made up of receive lines arrayed in the azimuth direction and identified in the drawing as L1, L2, . . . Ln, where "n" may be 128, for instance. In the view of FIG. 4, each receive line is being viewed axially as it would from the perspective of the transducer array. Rather than transmit a single transmit beam down each line and receive echoes from only that receive line, four receive lines are insonified by a single transmit beam. In the example of FIG. 4a a transmit beam TxA1, outlined radially, insonifies receive lines L1 and L2 of slice $S_1$ and receive lines L1 and L2 of slice $S_2$. Thus, two receive lines in azimuth and two receive lines in elevation, a total of four receive lines, are acquired simultaneously and processed. See, e.g., U.S. Pat. No. 5,318,033 (Savord) for an explanation of the processing of simultaneously received multilines. FIG. 4b illustrates the next transmit event, in which a transmit beam TxA2 insonifies another four receive lines, L3 and L4 of slice $S_1$ and receive lines L3 and L4 of slice $S_2$. Scanning proceeds in this manner until all of the lines of slices $S_1$ and $S_2$ have been acquired. Thus in the interval during which the full azimuth of a slice has been scanned, from line L1 through line Ln, echo data from two slices, $S_1$ and $S_2$, has been acquired. The process then continues with a second azimuth scanning interval as shown in FIG. 4c with the scanning of receive lines L1 and L2 of slice $S_3$ together with receive lines L1 and L2 of slice $S_4$ by transmit beam TxB1. Slices $S_3$ and $S_4$ are scanned during this second azimuth scanning interval in the same manner as slices $S_1$ and $S_2$ were acquired during the first. In these two scanning intervals all four slices $S_1$-$S_4$ are scanned in the time required to scan a single slice in the conventional line-by-line approach. The speed of acquisition and hence the frame rate of display have been increased by a factor of four by the use of this 4× multiline acquisition.

Figure 5:
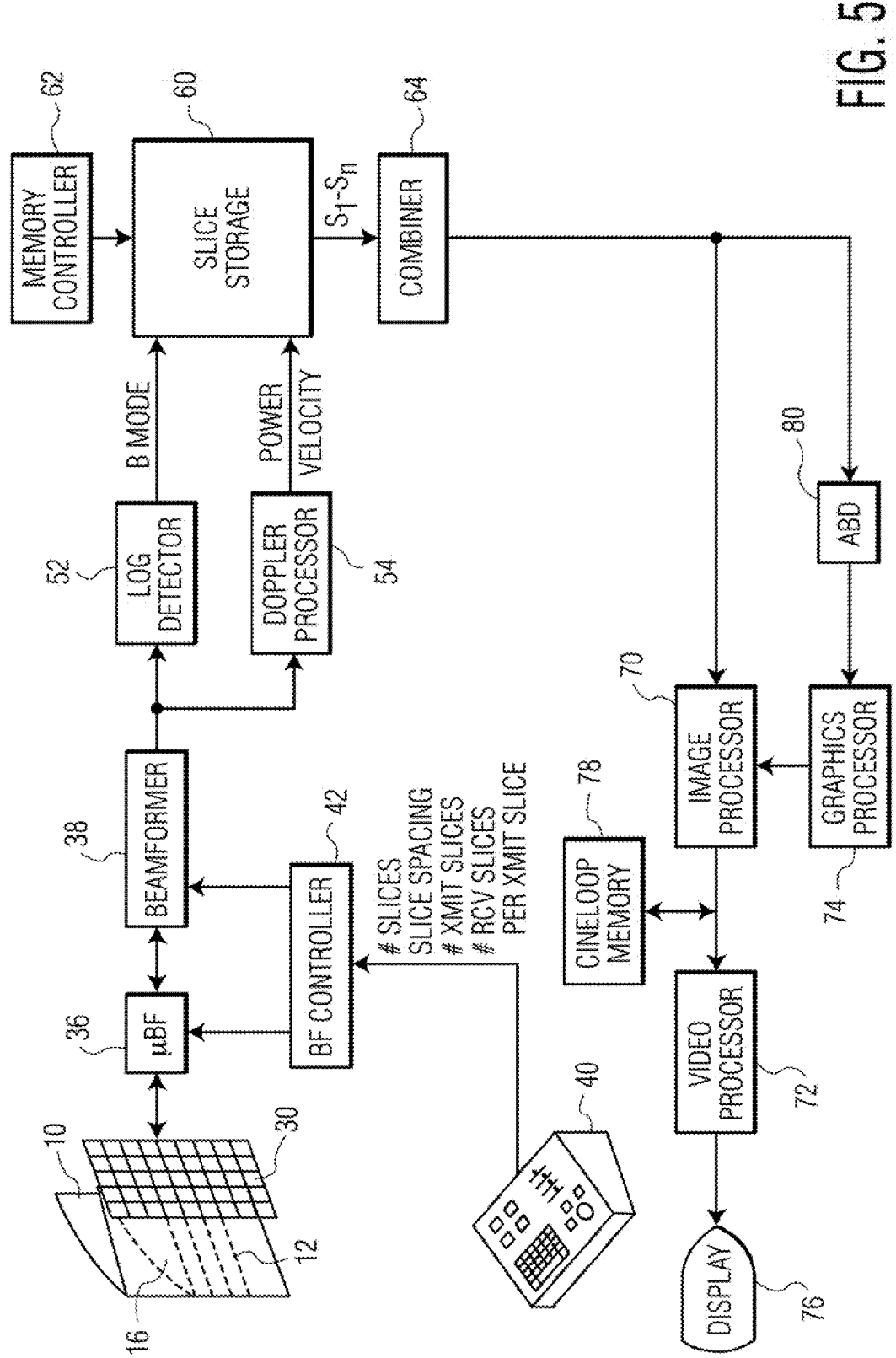
FIG. 5 illustrates in block diagram form an ultrasonic diagnostic imaging system constructed in accordance with the principles of the present invention.

An ultrasound system constructed in accordance with the principles of the present invention is shown in block diagram form in FIG. 5. A two dimensional array transducer 30 is provided which electronically steers and focuses beams over a volumetric region 10 under control of a microbeamformer 36, main beamformer 38, and beamformer controller 42. Alternatively, a one dimensional array transducer can be mechanically oscillated to scan the volumetric region. In this case the microbeamformer 36 located in the probe case with the 2D transducer array 30 controls the scanning of groups of elements called subarrays or patches in scanning a volumetric region 10. Partially beamformed signals from the microbeamformer 36 are formed into fully beamformed signals by the main beamformer 38. A beamformer controller 42 provides control signals for the beamformer and microbeamformer. Further details on microbeamformer-controlled scanning of volumetric regions may be found in U.S. Pat. No. 6,623,432 (Powers et al.), and U.S. Pat. No. 6,709,394 (Frisa et al.), PCT publication WO 2005/099579 (Rafter) and U.S. patent application 60/777,831 (Savord), filed Mar. 1, 2006. In this example a user control panel 40 is coupled to the beamformer controller 42 and is operated to control a number of parameters of the scanning of slices 12-16 of the volumetric region 10, including the number of slices to be scanned, the spacing between slices, the number of transmit slices, and the number of receive slices per transmit slice. Referring back to FIGS. 4a-4c, in that example the number of slices to be scanned was four, the spacing between slices was a specified angular or linear parameter, the number of transmit slices was two, and the number of receive slices per transmit slice was two.

The beamformed echo signals received from the scanned slices are detected by a log detector 52 for B mode imaging. Alternatively or in addition, the received echo signals may be Doppler processed by a Doppler processor 54 for the display of flow or motion in the image field. The B mode image data and the Doppler image data (e.g., Doppler power and/or velocity) of each slice are stored in slice storage buffer 60. Addressing of the buffer 60 to write data into the buffer or read data out of the buffer is controlled by memory controller 62. In an implementation of the present invention a plurality of elevationally different slices are read out of the slice storage buffer 60 and combined by a combiner 64.

The combiner 64 may combine the image data of multiple elevationally different slices in various ways. Combining is preferably performed on image data from different slices which have the same azimuth and depth coordinates in each slice. Alternatively, raylines can be mathematically projected through the multiple slices in the manner of raycasting for volume rendering. Preferably the raylines are projected normal to the planes of the slices. The image data intersected by each rayline is the data which is combined. In the combining process the image data can be averaged or can be summed and normalized. A mean or median value of the data values can be computed, or a peak value of the data being combined can be used. The data from the central slice can be weighted more greatly than the data of neighboring slices, with slice data being weighted in relation to its distance from the central slice. Slice data can be weighted in relation to its proximity to the viewer with slice data in the front of the volume being weighted more greatly than slice data in the back. The combined data thus forms a "thick slice" which can be displayed as a planar display of a slice with characteristics of multiple elevationally offset individual slices. The thick slice data is coupled to an image processor 70 for further processing such as scan conversion into the desired display format (e.g., sector or linear) and is processed into video signals by a video processor 72 for display on a display 76. The image data can also be saved or stored in a Cineloop® memory 78, harddrive or other image storage device. The thick slice display will exhibit reduced speckle artifacts as compared to an individual one of the acquired slices.

Figure 7A:
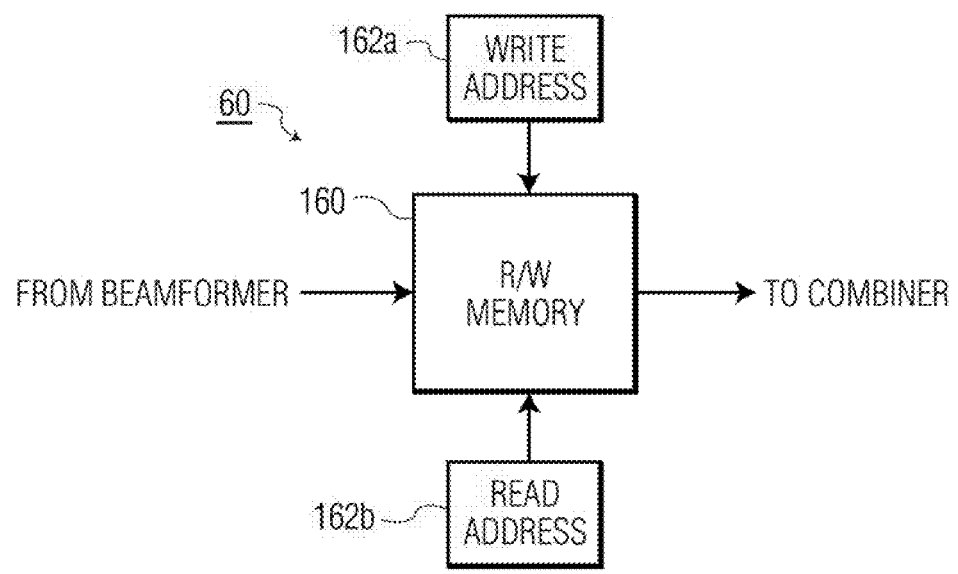
FIG. 7a illustrates a dual ported memory used for slice storage in an implementation of the present invention.
Figure 7B:
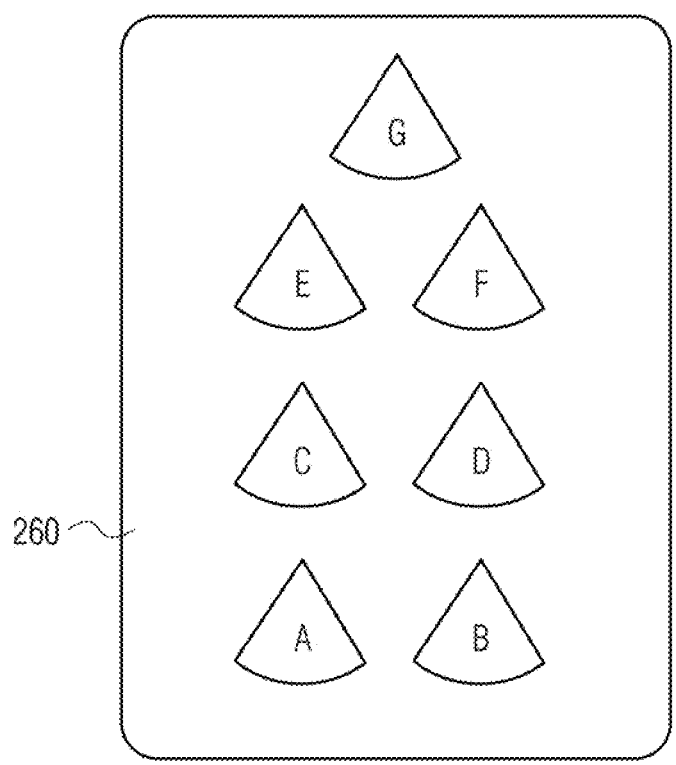
FIG. 7b illustrates partitioning of memory areas in an implementation of the present invention.

In accordance with a further aspect of the present invention a high frame rate of display for thick slice images may be obtained by means of the apparatus and techniques depicted in FIGS. 7a and 7b. FIG. 7a illustrates the slice storage buffer 60 implemented as a dual port memory 160 which can be written to and read from simultaneously. The use of such a R/W memory 160 enables the new data of a slice being scanned by the transducer array and beamformer to be written into one area of the R/W memory while the data of other slices previously stored in the memory is read out and combined to form a thick slice image. The writing of new slice image data into the memory 160 is controlled by a write address controller 162a while the reading of slice image data from other locations in the memory is under the control of a read address controller 162b. In this technique a new thick slice image can be combined for display while the image data from a new slice is being acquired. One example of the allocation of memory for a combined four-slice thick slice image is illustrated by FIG. 7b. The storage area 260 of the memory is shown to contain seven image storage areas labeled A through G.

An example employing the 4× multiline scanning technique of FIGS. 4a-4c for four component slices $S_1$-$S_4$ is as follows. Using the user interface 40, the ultrasound system is set to scan four slices with a given slice spacing, using two transmit slices and two receive slices per transmit slice. Scanning of the first two slices proceeds during a first scanning interval as shown in FIGS. 4a and 4b and the data of the two acquired slices $S_1$ and $S_2$ is written into memory areas A and B. Slices $S_3$ and $S_4$ are then scanned during a second interval and the data of these two slices is written into memory areas C and D. The transducer array and beamformer then begin to scan slices $S_1$ and $S_2$ again and write the data from the rescanning of slices $S_1$ and $S_2$ into memory areas E and F. While these slices are rescanned, the image data of memory areas A,B,C, and D is read out of the memory and coupled to the combiner 64 where the individual slice data is combined into a thick slice image. The resultant thick slice image is written into memory area G, from which it is read out and coupled to the image processor (and other components as described below) as needed for processing and display. In a typical implementation the time required to composite the thick slice image and process the image for display will take less time than the time required to rescan slices $S_1$ and $S_2$. After the rescanning of slices $S_1$ and $S_2$ is complete, the image data of slices $S_1$, $S_2$, $S_3$, and $S_4$ which is stored in memory areas C,D,E, and F is read out for combining into a new thick slice image for display, and the new thick slice image is written into memory area G to update the real time thick slice image. Simultaneously, slices $S_3$ and $S_4$ are rescanned and their slice data is written into memory areas A and B. In the next scanning interval iteration slices $S_1$ and $S_2$ are scanned again and their data written into memory areas C and D while the slice data of memory areas E,F,A, and B is combined to form another thick slice image to update the image in memory area G. This use of 4× multiline for slice acquisition and the combination of new slice data with the most recent data of the other slices of the thick slice image is seen to enable a frame rate of display of the thick slice image which is equal to that of a single slice scanned and displayed by conventional single line scanning. Thus, there would be no degradation of frame rate when changing from conventional single slice imaging to thick slice imaging of four component slices by this technique.

An implementation of the present invention has been found to be especially useful in colorflow imaging, particular for the detection of small, localized and intermittent flow conditions such as a heart valve jet. Colorflow has long been used in the detection of flow jets from valve leakage, a clinical application for which sensitivity far outweighs precise image resolution. Normally this procedure takes a long time as the clinician slowly moves the image plane around the heart valve, looking for a short burst of color characteristic of a jet. However, with the system of FIG. 5, this procedure is considerably enhanced. Since the combiner combines a number of elevationally distinct planes spread over a small volumetric region in elevation, the jet need not occur in the center plane in order to be detected. The occurrence of a jet in the plane of an adjacent slice which is collapsed into the thick slice will enable the jet to be detected even when it is not present in the central slice plane of the thick slice. Furthermore, the jet is more easily detected by the reduction of speckle artifact and color dropout in the thick slice image. While the processing of one of the component slices by the Doppler processor 54 may result in black holes in the colorflow image where destructive interference from the speckle pattern has manifested itself, the differing speckle pattern of the neighboring slice may not exhibit this problem at the same point in the image. Thus, when the colorflow slices are combined in the elevation dimension into the thick slice image, the black hole of one slice may be filled in by valid colorflow of a neighboring slice. The colorflow field will appear smoother and more sensitive to out-of-central plane jets with less far field degradation. Sensitivity of the procedure to jet detection is accordingly enhanced.

For the production of a Doppler thick slice image, ensembles of echo signals are received from locations where flow or motion is present and are processed by the Doppler processor 54 to produce a Doppler estimate at those locations. The Doppler estimate may be one of Doppler power at the location, or velocity or variance. Corresponding B mode images may also be acquired if desired so that the Doppler information may be overlaid on structural detail framing the motion. The Doppler slice images are stored in slice storage 60, then combined by combiner 64 using a selected combining technique. Defects in the flow or motion display due to speckle or dropout are thereby reduced, and flow or motion defects in adjacent slice planes are more easily identified by the projection of multiple Doppler slices in the elevation dimension. Furthermore, since the acquisition of multiple temporally different samples from each flow or motion location will decrease the frame rate of acquisition in the Doppler mode, at least some of this frame rate degradation may be overcome by use of the high speed thick slice display technique discussed in conjunction with FIGS. 7a and 7b above.

In accordance with a further aspect of the present invention, the thick slice images are also coupled to an automated or semi-automated border detector (ABD) 80. As is well known, border detectors are used to identify tissue borders in ultrasound images. The border detectors can operate with initial user involvement to identify points on one border in one image, then use that input to automatically identify the full border and the border in other images of a real time image sequence. Other border detectors operate automatically by identifying tissue landmarks in an image then drawing borders using those landmarks. See, for example, U.S. Pat. No. 6,491,636 (Chenal et al.) and U.S. Pat. No. 6,447,453 (Roundhill et al.) and US patent publication 2005/0075567 (Skyba et al.) The border detector 80 identifies a tissue border in a thick slice image with or without user assistance (semi-automated or automated) and couples data identifying the location of the border in one or more thick slice images to a graphics processor 74. The graphics processor 74 creates a graphic outline of the border to the image processor 70 which overlays the identified border over the corresponding thick slice image. It has been found that automated or semi-automated border detection performs better on thick slice images than on comparable single slice images. This is because a tissue border defined by thin tissue which is not a strong reflector of ultrasonic echoes such as the endocardial border of the myocardium can produce a poorly defined tissue border in a single slice image. Image dropout at the border region can produce an ill-defined image border which is difficult to trace reliably by an automated or semi-automated process. In addition, the poorly-defined border can be further disrupted by the image speckle pattern. The combining of elevationally distinct images into a thick slice image can reduce the speckle artifact and make the border more distinct in the image. In addition, missing border segments in one slice can be augmented by identifiable border segments in adjoining slices, causing the consolidated tissue border of the thick slice image to be more clearly defined and hence more reliably processed and identified by the border detector 80.

In accordance with a further aspect of the present invention, thick slice imaging is used in the diagnosis and quantification of perfusion defects with the aid of ultrasonic contrast agents. When a contrast agent is present in a blood pool such as a blood vessel or chamber of the heart, the contrast agent will generally be present in considerable volume and density in the blood pool. The relatively high concentration of the microbubbles of the contrast agent enable quick and reliable detection of its presence in an ultrasound image. However in perfusion studies such as those conducted with contrast agents to detect poorly perfused tissue such as myocardial tissue which has been infracted, the contrast agent is only present in small amounts in the tiny capillaries which perfuse the tissue. This low concentration of the microbubbles often makes their detection and quantification difficult or unreliable. This is at a time when high resolution is required since perfusion defects often show up as thin subendocardial regions of slower filling as well as potentially lower blood volume. In addition, perfusion studies are generally conducted at low transmit power levels to avoid breaking or disrupting the microbubbles in the capillary bed and causing them to disappear. Consequently the signal-to-noise ratio of the perfusion images is relatively low, frequently by as much as 20 dB lower than standard imaging techniques, causing further degradation in resolution. The resultant images can have a display dynamic range which is 20 dB or more lower than conventional images without contrast, causing the speckle artifact to have a more pronounced adverse impact on image resolution and the detection of subendocardial regions of poor perfusion.

Accordingly, contrast images for perfusion diagnosis and/or quantification are improved in accordance with the present invention by scanning multiple planes in the elevation dimension and projecting these multiple elevation slices in the elevation dimension. By performing such operations it is possible to reduce speckle without sacrificing resolution and signal to noise. The methods for compositing or combining slices which have been described above may be employed, including simple averaging and maximum intensity projection, or using compositing techniques from volume rendering (e.g., raycasting). By performing these techniques, the contrast agent speckle will be greatly reduced, subendocardial defects will be more evident, and quantification techniques such as parametric imaging will yield better results. Furthermore, since "destruction-replenishment" techniques require exactly the same elevation slice to be maintained for 10 seconds or more, thick-slice imaging will be more robust in the presence of small movements of the probe, since a plurality of adjacent slices are used to form the thick slice image plane. Thus, slight movement of the probe to different slice locations will have only minimal effect on the results obtained.

Figure 6:
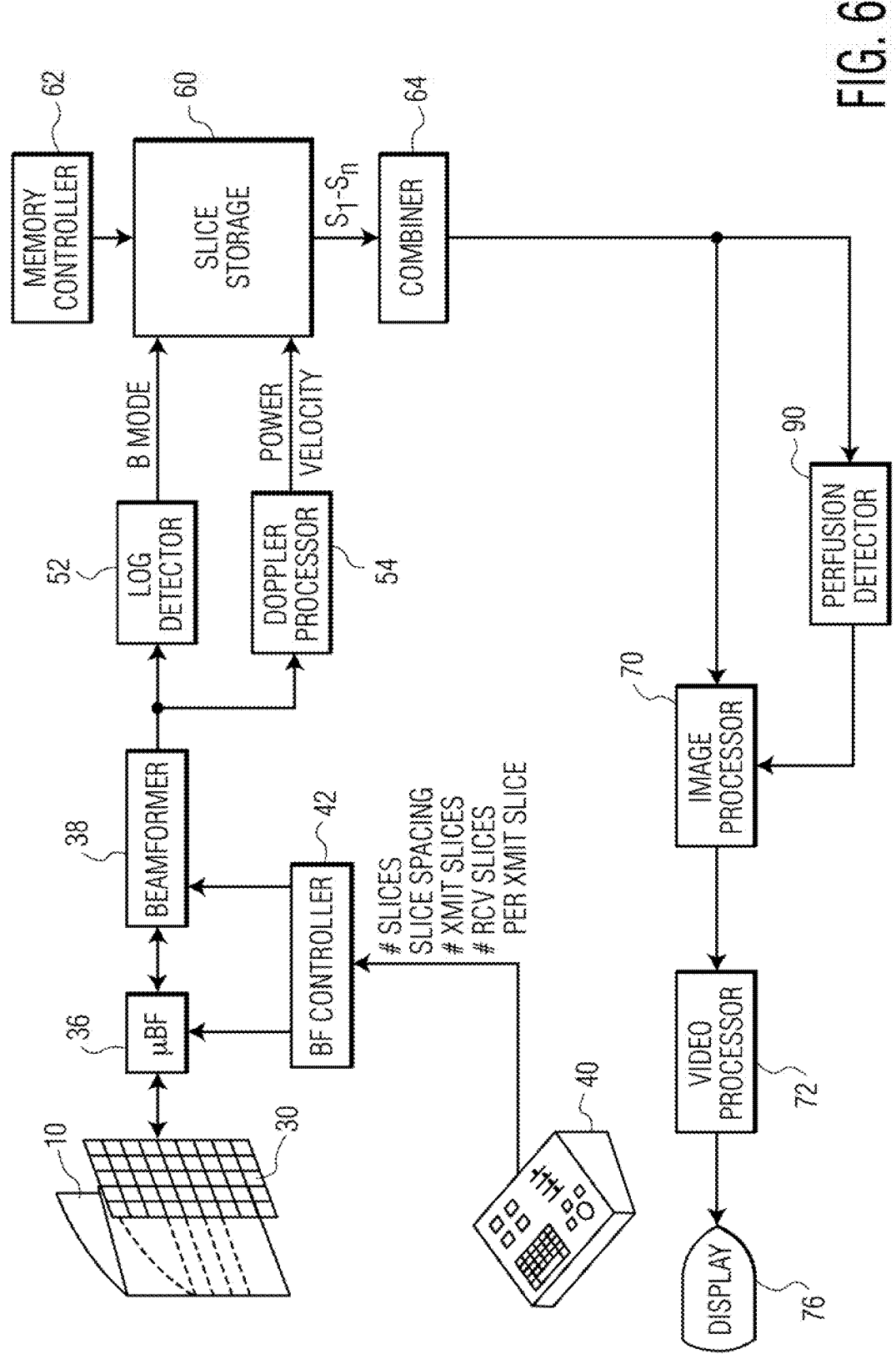
FIG. 6 illustrates in block diagram form a second implementation of an ultrasonic diagnostic imaging system constructed in accordance with the principles of the present invention.

An ultrasound system constructed in accordance with the principles of the present invention for perfusion studies is shown in block diagram form in FIG. 6, in which elements previously described in conjunction with FIG. 5 are identified by the same reference numerals. In this system thick slice images of microbubble-perfused tissue which are produced by the combiner 64 may be processed as B mode images by the image processor 70, the video processor 72, and the display 76 for the display of real time grayscale images of perfusion which exhibit better resolution of tissue perfusion by virtue of reduced speckle caused by the elevational slice combining process. In this example the thick slice contrast images are also coupled to a perfusion detector 90. The perfusion detector 90 may be constructed in the same manner as the contrast signal, detector described in PCT publications WO 2005/044108 (Rafter) and WO 2005/099579 (Rafter) to detect and enhance the display of contrast agent perfusion in the images. Alternatively or in addition the perfusion detector may be configured as the contrast signal detector described in U.S. Pat. No. 6,692,438 (Skyba et al.) to produce a color overlay of the B mode image which depicts perfused tissue in a qualitative color display, or a quantitative display of a perfusion curve or curve parameter for different points in the image.

Other variation of the present invention will readily occur to those skilled in the art. For example, the concepts of the present invention may be employed in an implementation which does not use multiline acquisition but acquires one receive line for every transmitted scanline. Various sequence of line acquisition may be employed other than successive acquisition of adjacent lines such as those shown in U.S. Pat. No. 5,438,994 (Starosta et al.) and U.S. Pat. No. 5,617,863 (Roundhill et al.) Higher order multiline may be employed than the illustrated 4× multiline, including a multiline order which acquires all of the component slices in one azimuthal scan sequence. Doppler modes other than colorflow may use the present invention including spectral Doppler, flow variance, and color M mode. M mode may use an implementation of the present invention which acquires and combines spatially distinct M lines into one display M line. The techniques of the present invention are applicable to both fundamental and harmonic imaging.

What is claimed is:

1. An ultrasonic diagnostic imaging system for thick slice imaging comprising:
   an array transducer configured to transmit and receive scanlines over a volumetric region;
   a beamformer, coupled to the array transducer, which acts to control the array transducer to transmit beams, each of which insonifies a plurality of receive scanline locations, and to receive echoes from the plurality of receive scanline locations simultaneously to produce image data of a plurality of parallel, elevationally distinct slices of the volumetric region;
   a slice memory, coupled to the beamformer, which stores slice image data;
   a combiner, coupled to the slice memory, which combines newly acquired slice image data with a portion of previously acquired slice image data in the elevation direction; and
   a display responsive to the combiner for displaying thick slice images at a frame rate which is faster than that of the time to acquire a complete set of the combined slice image data.

2. The ultrasonic diagnostic imaging system of claim 1, further comprising a beamformer controller coupled to the beamformer which controls the number of slices to be scanned for a thick slice image.

3. The ultrasonic diagnostic imaging system of claim 2, wherein the array transducer is configured to electronically focus and steer scanlines over a volumetric region.

4. The ultrasonic diagnostic imaging system of claim 3, wherein the beamformer further comprises a multiline beamformer.

5. The ultrasonic diagnostic imaging system of claim 4, wherein the beamformer controller further controls at least one of the number of transmit slices and the number of receive slices per transmit slice.

6. The ultrasonic diagnostic imaging system of claim 1, wherein the slice memory includes a first memory area for storing data of a currently acquired slice and a second memory area for storing data of previously acquired slices which are to be combined in a thick slice image.

7. The ultrasonic diagnostic imaging system of claim 6, wherein the slice memory further includes a third memory area for storing data of a thick slice image.

8. The ultrasonic diagnostic imaging system of claim 1, wherein the combiner further performs at least one of summing slice data in the elevation direction, averaging slice data in the elevation direction, weighting slice data in the elevation direction, or detecting the maximum value of slice data in the elevation direction.

9. The ultrasonic diagnostic imaging system of claim 1, wherein the slice image data is processed prior to storage in the slice memory by at least one of a B mode processor or a Doppler processor.

10. The ultrasonic diagnostic imaging system of claim 1, wherein the beamformer further comprises a microbeamformer coupled to the array transducer and a main beamformer coupled to the microbeamformer.

11. An ultrasonic diagnostic imaging system for thick slice imaging comprising:
   an array transducer located in an ultrasound probe and configured to transmit and receive scanlines over a volumetric region;
   a microbeamformer located in the probe and coupled to the array transducer to control the array transducer to transmit beams, each of which insonifies a plurality of receive scanline locations, and to receive echoes from the plurality of receive scanline locations simultaneously, and to further control the steering and focusing of ultrasound signals over a plurality of adjacent slices in the volumetric region which are parallel to each other in the elevation direction;
   a detector, coupled to the microbeamformer, which detects image data of the slices;
   a slice memory, coupled to the beamformer, which stores slice image data;
   a combiner, coupled to the slice memory, which combines recently acquired slice image data with slice image data previously combined with other slice image data in the elevation direction; and
   a display responsive to the combiner for displaying thick slice images at a real time frame rate of display which is faster than that of the time to acquire the recently acquired and the previously combined slice image data.

12. The ultrasonic diagnostic imaging system of claim 11, wherein the array transducer comprises an electronically steered and focused two dimensional array transducer.

13. The ultrasonic diagnostic imaging system of claim 12, wherein the array transducer acts to transmit beams, each of which insonifies receive scanline locations of a plurality of slices.

14. The ultrasonic diagnostic imaging system of claim 13, wherein the array transducer scans a slice by transmitting beams over an azimuth scanning interval, and wherein the array transducer acquires echo signals from a plurality of slices during the azimuth scanning interval.

15. The ultrasonic diagnostic imaging system of claim 14, wherein the detector detects image data of the plurality of slices, and
   wherein the slice memory operates to store the image data of the plurality of slices.

16. The ultrasonic diagnostic imaging system of claim 15, wherein, following the azimuth scanning interval, the combiner acts to combine in the elevation dimension the image data of the plurality of slices acquired during the azimuth scanning interval with the image data of a plurality of previously acquired slices.

17. The ultrasonic diagnostic imaging system of claim 15, wherein following the azimuth scanning interval, the array transducer commences a second azimuth scanning interval, during which echo signals are acquired from a second plurality of slices,
   wherein the slice memory operates to store image data from the second plurality of slices in place of at least some of the image data of the previously acquired slices.

18. The ultrasonic diagnostic imaging system of claim 17, wherein, following the second azimuth scanning interval, the combiner acts to combine in the elevation dimension the image data of the slices acquired during the first and second azimuth scanning intervals.

* * * * *